United States Patent [19]
Wang et al.

[11] Patent Number: 5,532,132
[45] Date of Patent: Jul. 2, 1996

[54] METHOD FOR REGULATING FORMATION OF A COMPLEX OF PLASMINOGEN ACTIVATOR, ITS RECEPTOR AND INHIBITOR

[75] Inventors: Ning Wang, Wuhan, China; Georgia Barlovatz-Meimon, Paris, France; Jeffrey J. Fredberg, Sharon, Mass.

[73] Assignees: President and Fellows of Harvard University, Cambridge, Mass.; University of Paris, France

[21] Appl. No.: 127,977

[22] Filed: Sep. 28, 1993

[51] Int. Cl.$^6$ .................................................. G01N 33/567
[52] U.S. Cl. ..................... 435/7.21; 435/7.23; 435/7.9; 436/501; 436/503
[58] Field of Search ................................. 435/7.21, 7.23, 435/7.9, 13, 24; 436/503, 501

[56] References Cited

PUBLICATIONS

J. Behrens, et al., *J. Cell Biol.*, 108:2435 (1989).
J. Folkman, et al., *Nature*, 273:345 (1978).
D. Inger, *Proc. Natl. Acad. Sci., USA* 87:3579 (1990).
M. Bissel, et al., *J. Theor. Biol.*, 99:31 (1982).
Mooney, et al., *J. Cell Physiol.*, 151:497 (1992).
D. Ingber, *Am. J. Path.*, 122:129 (1986).
D. Ingber, *Proc. Natl. Acad. Sci., USA* 78:3901 (1981).
D. Ingber, et al., *J. Cell. Biol.*, 109:317 (1989).
F. Blasi, *BioAssays*, 15:105 (1993).
K. Dano, et al., *Adv. Cancer Res.*, 44:139 (1985).
L. Naldini, et al., *EMBO, J.*, 11:4825 (1992).
P. H. A. Quaz, et al., *Fibrinolysis*, 6:41 (1992).
P. H. A. Quax, et al., *Cell Regulation*, 2:793 (1991).
J. Pollanen, et al., *Adv. Cancer Res.*, 57:273 (1991).
A. P. Sappino, et al., *J. Cell Biol.*, 109:2471 (1989).
J. F. Cajot, et al., *J. Cell Biol.*, 109:915 (1989).
V. H. Hearing, et al., *Cancer Res.*, 48:1270 (1988).
L. Ossowski, *J. Cell Biol.*, 107:2437 (1988).
A. P. Sappino, et al., *J. Clin. Invest.*, 88:1073 (1991).
L. Ossowski, et al., *Cell*, 35:611 (1983).
J. F. Cajot, et al., *Proc. Natl. Acad. Sci. USA*, 87:6939 (1990).
L. Ossowski, et al., *Cancer Res.*, 51:274 (1991).
B. L. Bergman, et al., *Proc. Natl. Acad. Sci., USA*, 83:996 (1986).
A. Estreicher, et al., *J. Cell Biol.*, 111:783 (1990).
D. A. Waltz, et al., *J. Clin. Invest.*, 91:1541 (1993).
Frixen and Nagamine, *Cancer Res.*, 33:3618–3621 (1993).
Jensen and Wheelock, *Exp. Cell. Res.*, 202:190–198 (1992).
Henderson, et al., *Science*, 254:1131 (1991).
Weinberg, *Science*, 254:1138 (1991).
Aaronson, *Science*, 254:1146 (1991).
Solomon, et al., *Science*, 254:1153 (1991).
Adams and Cory, *Science*, 254:1161 (1991).
Hausen, *Science*, 254:1167 (1991).
Pastan and Fitzgerald, *Science*, 254:1174 (1991).
Ingber, *Nature*, 348:555 (1990).
Olsen et al., "Internalization of the Urokinase–Plasminogen Activator Inhibitor Type–I Complex is Mediated by Urokinase Receptor", *J. Biol. Chem.* vol. 267, No. 13, pp. 9129–9133, (1992).

*Primary Examiner*—Toni R. Scheiner
*Assistant Examiner*—Susan C. Wolski
*Attorney, Agent, or Firm*—David G. Conlin; David S. Resnick; Dike, Bronstein, Roberts & Cushman

[57] ABSTRACT

The present invention is directed to a method for regulating formation of a complex of a plasminogen activator, its receptor and one of its inhibitors. More specifically, this method involves contacting a target cell having a plasminogen activator receptor with a compound which interacts with a component of the complex such that a change in target cell cytoskeletal stiffness results.

2 Claims, 3 Drawing Sheets

METHOD FOR REGULATING FORMATION OF A COMPLEX OF PLASMINOGEN ACTIVATOR, ITS RECEPTOR AND INHIBITOR

The United States Government has rights in this invention by virtue of the National Heart, Lung and Blood Institute grant P01 HL 33009.

The present invention is directed to a method for regulating formation of a complex of a plasminogen activator, its receptor and one of its inhibitor. More specifically, this method involves contacting a target cell having a plasminogen activator receptor with a compound which interacts with a component, or more than one component of the complex such that a change in target cell cytoskeletal stiffness results.

BACKGROUND OF THE INVENTION

Adherent mammalian cells cultured in vitro are typically removed from the culture surface by use of trypsin, a protease which cleaves molecules involved in adherence. However, it has be found that after several treatments with trypsin, the cells become non-adherent and lose some normal functions. Additionally, the addition of a protease to a cell culture may cause other cellular damage, and if possible should be avoided. However, few alternatives are available.

The invasive potential of a cancer cell is extremely important. The traditional method of looking at such invasive potential of living cells is by using in vitro assays. This requires an in vitro assay and it typically takes about 3 weeks for results to be obtained [J. Behrens, et al., J. Cell Biol., 108:2435 (1989)]. This can be an extremely long time period where rapid diagnosis is desired. Accordingly, it would be desirable if there was a rapid method for assaying cells for their invasive potential.

Control of cell shape by extracellular matrix (ECM), molecules outside the cell, is critical for regulation of cell growth [J. Folkman, et al., Nature, 273:45 (1978); D. Ingber, Proc. Natl. Acad. Sci. U.S.A., 87:3579 (1990)] differentiation [M. Bissel, et al., J. Theor. Biol., 99:31 (1982); Mooney, et al., J. Cell Physiol., 151:497 (1992)] cell polarity [D. Ingber, et al., Am. J. Path., 122:129 (1986)] and tissue pattern formation [D. Ingber, et al., Proc. Natl. Acad. Sci. U.S.A., 78:3901 (1981); D. Ingber, et al., J. Cell. Biol., 109:317 (1989)]. These functions depend on the close cooperation of the ECM, protein on the surface of the cell, for example, cell adhesion molecules such as integrins, and proteins inside the cell, including the proteins of the cytoskeleton (CSK).

CSK structure has been shown to be associated with, for example, cell motility, differentiation, mitosis and adhesion. [T. P. Stossel, Science, 260:1086 (1993); J. S. Hyams, and B. R. Brinkley, eds. "Mitosis: Molecules And Mechanisms," Academic Presss, San Diego (1989).] The function of CSK structure is tightly coupled to CSK mechanical properties. One very important parameter of CSK mechanical properties is CSK stiffness. Accordingly, the ability to regulate or control the cytoskeletal stiffness of cells, both in vivo and in vitro, is important not only to advance understanding of the relationship between CSK structure and cell function, but also to identify agents that can be used to regulate functions related to the CSK. Agents commonly used to alter the structure of the CSK are cytotoxic and destructive. Such agents include cytochalasin D (or B) to disrupt actin microfilaments, nocodazole or colchicine to disrupt microtubules and acrylamide to disrupt intermediate filaments.

Control of the integrity of the ECM is believed to be a balance of proteases and anti-proteases. Urokinase (uPA), a plasminogen activator can play a regulatory role in the breakdown of ECM [F. Blasi, BioEssays, 15:105 (1993)]. uPA can cleave at least two precursor proteins: plasminogen to form plasmin, pro-hepatocyte growth factor to form hepatocyte growth factor [K. Dano et al., Adv. Cancer Res., 44:139 (1985); L. Naldini, et al., EMBO, J., 11:4825 (1992)]. Transformed cells and tumor cells have been shown to secrete increased amounts of urokinase plasminogen activator (uPA) [F. Blasi, Bioessays, 15:105 (1993); P. H. A. Quax, et al., Fibrinolysis, 6:41(1992); P. H. A. Quax, et al., Cell Regulation, 2:793 (1991); J. Pollanen, et al., Cancer Res., 57:273 (1991); A. P. Sappino, et al., J. Cell Biol., 109:2471 (1989); J. F. Cajot, et al., J. Cell Biol., 109:915 (1989); V. H. Hearing, et al., Cancer Res., Cancer Res., 48:139 (1988); L. Ossowski, J. Cell Biol., 107:2437 (1988); K. Dano, et al., Adv. Cancer Res., 44:139 (1985); A. P. Sappino, et al., J. Clin. Invest., 88:1074 (1991)]. The role of uPA in cell invasion is thought to involve activation of plasminogen and the subsequent formation of plasmin, as well as degradation of extracellular matrix (ECM). Thus, uPA can help cells to loosen adhesions to ECM, thereby permitting invasion of other tissues. The activity of plasmin and that of uPA are correlated with tumor invasion and metastasis, while inhibitors can block the ECM degradation by tumor cells [P. H. A. Quax et al., Fibrinolysis, 6:41 (1992); A. P. Sappino, et al., J. Clin. Invest. supra; L. Ossowski, et al., Cell, 35:611 (1983); J. F. Cajot, et al., Proc. Natl. Acad. Sci. U.S.A., 87:6939 (1990); L. Ossowski, et al., Cancer Res., 51:274 (1991); B. L. Bergman, et al., Proc. Natl. Acad. Sci. U.S.A., 83:996 (1986)]. Furthermore, in normal cells, the uPA receptor (uPAR) and uPA have also been found at the leading edge of migrating monocytes [A. Estreicher, et al., J. Cell Biol., 111:783 (1990)]. Very recently, cell adhesion in myeloid cells was increased when the uPA/uPAR system was blocked independent of its proteolytic function (D. A. Waltz, et al., J. Clin. Invest., 91:1541 (1993)]. The role of the uPAR-uPA system in cell movement suggests a possible association of the uPA enzymatic system with the cytoskeleton (CSK) [Frixen and Nagamine, Cancer Res., 33:3618–3621 (1993); Jensen and Wheelock, Exp. Cell. Res., 202:190–198 (1992)]. However, no method has been developed which allows regulation of the CSK via the uPA system.

Decontrolled cell growth, decreased cell adhesion, increased cell invasion, and transformed differentiation are a hallmark of malignant transformation. While research data have shown that there are many causative agents [Tomatis, WHO, Internat. Agency for Research on Cancer, Sci. Publ. 100, Lyon, France, (1990)], there are few effective methods which can be used to inhibit abnormal cell growth or to decrease cancer metastasis. Currently, commonly-used methods for inhibiting abnormal cell growth include cell killing with toxins conjugated with monoclonal antibodies to target cancer cells directly or with recombinant toxins, intervening signaling pathways for growth factors, activate or insert tumor suppressor genes, chemotherapy, antiviral therapy [Henderson, et al., Science, 254:1131 (1991); Weinberg, Science, 254:1138 (1991); Aaronson, Science, 254:1146 (1991); Solomon, et al., Science, 254:1153 91991); Adams and Cory, Science, 254:1161 (1991); Hausen, Science, 254:1167 (1991); Pastan and Fitzgerald, Science, 254:1174 (1991)]. Other indirect ways to inhibit abnormal cell growth is the inhibition of anglogenesis to deprive cancer cells of nutrients [Ingber, et al., Nature, 348:555 (1990)]. However, there are very few methods which target specifically intracellular primary structures (the cytoskeleton) to inhibit cell growth and/or cell invasion.

It would be desirable to have a method which can be used to detach adherent cells cultured in vitro without the use of proteases.

It would be desirable to have a simple method of diagnosis of invasive potential of cells.

It would be desirable to have an assay that could be used in vitro to more rapidly determine the invasive potential of cells.

It would be desirable to have an assay that could be used in vivo to determine invasive potential of cells.

It would be desirable to have a method by which one could measure the change in invasive potential of particular tissues.

It would be desirable to have a method which can be used to regulate cellular cytoskeletal stiffness without the use of cytotoxic agents.

It would be desirable to have a method which can be used to readily screen and select compounds that are capable of regulating cellular cytoskeletal stiffness, and thus can be used to regulate functions related to the CSK, for example, cell growth, mitosis, motility, invasion and differentiation.

SUMMARY OF THE INVENTION

Cells having plasminogen receptors are capable of forming a complex with an activator and an inhibitor. We have now discovered that formation of the complex effects the motility of the cell. Furthermore, this complex effects the cell's cytoskeletal stiffness. By looking at changes in this complex or the effects of such complex on cytoskeletal stiffness, one is able to assay the invasive potential of a cell. In accordance with the present invention, it has been found that one can use a simple in vitro assay, wherein one takes the cell of interest, plates it, treats the cell with a compound that interacts with the complex, for example, that blocks the inhibitor component of the complex, for example, an antibody to the inhibitor, and then assess cytoskeletal stiffness. Cells which are responsive to the blocking, i.e., those which show an increase in stiffness, have a higher invasive potential.

Similarly, one can use in vitro or in vivo assays to look for formation of the complex or changes in the complex to determine if the cells are acting or ready to act in an invasive manner.

We have also discovered a method by which one can regulate, i.e., inhibit, enhance or reverse, the formation of a complex of a plasminogen activator, its receptor and one of its inhibitor such that a change in target cell cytoskeletal stiffness results. Plasminogen activators useful in the method of the present invention include, for example, tissue plasminogen activator (tPA) and urokinase (uPA). The method of the present invention comprises contacting a target cell having a plasminogen activator receptor with an effective amount of a compound which interacts with a component of the complex such that a change in target cell cytoskeletal stiffness results. Compounds which interact with the complex components include, for example, complex components or modified versions thereof, complex component antagonists or agonists, antibodies against the complex components or against the whole complex and receptor decoys. In certain embodiments, more than one compound can be contacted with the target cell. In other embodiments, the compound reversibly interacts with a component of the complex.

In accordance with the present invention, it has been found that inhibiting the formation of the complex results in an increase in cytoskeletal stiffness, and thus, downregulation of cell migration and proliferation, and upregulation of cell adhesion. Whereas enhancing formation of the complex results in a decrease of cytoskeletal stiffness, and thus upregulation of cell migration, and downregulation of cell adhesion. Accordingly, the method of the present invention can be used both in vitro and in vivo to regulate cytoskeletal stiffness and thus regulate functions related to the cytoskeleton, such as cell adhesion, motility, migration, invasion, proliferation and differentiation. Unlike the above discussed agents commonly used to alter CSK structure, the method of the present invention is not cytotoxic and is reversible. In addition, with the present invention, it is not necessary that the compound enter the cell to influence CSK structure.

Stiffened target cells produced in accordance with the present invention may be used to select compounds, including drugs, that reverse changes in cytoskeletal stiffness and thus may be useful as agents for increasing cellular motility.

The present invention further includes methods for screening and selecting compounds that interact with the formation of the complex and thus may be used to regulate the cytoskeletal system.

The present invention further permits losing adhesion of cultured cells to the cell surface so they can be readily removed from such surface without the use of harsh reagents such as trypsin. Furthermore, the present invention includes methods for enhancing adhesion of a cultured cell line to a cell surface.

Preferred target cells are cells having a plasminogen activator receptor. Such cells include, for example, invasive or non-invasive cells, migrating cells, proliferating cells, differentiating cells, cells undergoing the process of interaction with other cells, and cells assembling into multicellular structures.

DETAILED DESCRIPTION OF THE INVENTION

The present invention is directed to a method of identifying and regulating i.e., inhibiting, enhancing or reversing, the formation of a complex of a plasminogen activator, its receptor and its inhibitor. For example, the upregulation or downregulation of the complex is an indication of the invasive potential of a cell. Additionally, by regulating the formation of the complex, the cytoskeletal stiffness of the target cell can be effected.

One method of the present invention comprises contacting a target cell having a plasminogen activator receptor with an effective amount of a compound which interacts with a component of the complex such that a change in target cell cytoskeletal stiffness results. In certain embodiments, the compound reversibly interacts with a component of the complex.

Another embodiment involves assaying target cells to determine their invasive potential, and changes in such invasive potential.

Target cells useful in the method of the present invention are cells possessing a plasminogen activator receptor. Plasminogen activators include tissue plasminogen activator (tPA) and urokinase (uPA). Cells possessing a plasminogen activator receptor can be readily identified using, for example, antibodies against the plasminogen activator receptor, using known methods (Stoppelli, et al., *Cell*, 45:675 (1986); Behrendt, et al., *J. Biol. Chem.* 265:6453 (1990).

Such cells include, for example, invasive (M6) or non-invasive cells (M7), migrating cells, proliferating cells, differentiating cells (myogenic cells), cells undergoing the process of interaction with other cells (for example, monocytes, neutrophils, interacting with endothelial cells in the process of migrating to peripheral tissues), and cells assembling into multicellular structures (for example trophoblast).

Preferred target cells are myogenic cells, endothelial cells, monocytes, macrophages, carcinoma cells, smooth muscle cells, neutrophils, fibroblast and epithelial cells, keratinocytes.

If necessary, the amount of target cell plasminogen activator receptor, plasminogen activator, and inhibitor, e.g., uPAR, uPA and $PAI_2$ can be increased by treating the target cells with cytokines such as transforming growth factor type β-1 ($TGF-\beta_1$), interleukin-1 (IL-1), and interleukin-2 (IL-2) [D. A. Waltz, et al., *J. Clin. Invest.*, 91:1541 (1993); M. R. Gyetko, et al., *J. Leuko. Biol.*, 53:598 (1993)]. Treatment with cytokines may be used to facilitate complex formation.

As used herein, the term "compound" refers to any agent, e.g., protein, chemical or drug, that interacts with a component of the complex such that formation of the complex is inhibited or enhanced. Such compounds may include, for example, complex components or modified versions thereof, complex component antagonists or agonists, receptor decoys and antibodies having specific affinity for one of the components of the complex such that the antibody binding interferes with the formation, functionality, and possible internalization of the complex. Antibodies against the complex per se are also suitable.

Complex components include a plasminogen activator, its receptor and one of its inhibitor. Plasminogen activators useful in the method of the present invention include urokinase (uPA) and tissue plasminogen activator (tPA). uPA is preferred. uPA and tPA are available commercially (American Diagnostica). Plasminogen activator inhibitors such as the uPA inhibitor $PAI_1$ are also available commercially (American Diagnostica). Plasminogen activator receptor has been purified and cloned. [N. Behrendt, et al., *J. Biol. Chem.* 265:6433 (1990); A. L. Roden, et al., *EMBO J.*, 9:467 (1990); A. D. Borglum et al., *Am. J. Hum. Genet.*, 50:492 (1992)]

Complex components may be modified using standard genetic engineering techniques to alter the components ability to inhibit or enhance complex formation. For example, a complex component may be modified to increase binding affinity with other components and thus encourage complex formation. This can be accomplished using random or site-directed mutagenesis. For example, the DNA encoding the complex component may be obtained using standard genetic engineering techniques. Single-stranded DNA is then prepared and used as a template for oligonucleotide-directed mutagenesis as described by Kunkel, et al., *Meth. Enzymology*, 154:367–382 (1987). Mutants that exhibit higher affinity for complex component, e.g., the receptor, can be screened and selected by comparing the effects of the mutant with the native in the formation of the complex. Additionally, desired mutants can be readily selected using a recombinant phage system (see, for example, McCafferty, et al., *Nature* 348:552–554 (1990); WO92/01047 and WO92/20791) or the directed evolution technique (U.S. Pat. No. 5,223,409).

Compounds also include receptor antagonist and agonists. Antagonist are compounds that bind to the receptor and block complex formation. Whereas agonists bind to the receptor and promote complex formation. A preferred antagonist or competitor is the urokinase amino terminal fragment (ATF) [Stoppelli, et al., *Proc. Natl. Acad. Sci. U.S.A.*, 82:4939 (1985]. Fragments from 20–150 amino, acids are suitable. The preferred fragment is 143 amino acids.

Receptor decoys may also be used to inhibit complex formation. Such decoys may be prepared by using receptor fragments that can not anchor to the cell membrane. Fragments may be obtained by use of standard genetic engineering techniques.

Antibodies against the complex components may also be used as compounds that inhibit complex formation. As used herein, the term "antibody against a complex component" refers to an antibody, monoclonal or polyclonal, or immunoactive fragments thereof, that has binding affinity for a complex component and is capable of inhibiting formation of the complex. Preferably, the antibody is directed to a domain that is associated with complex component binding. One such domain is the urokinase catalytical domain, or the receptor binding domain.

Antibodies that will specifically bind to the entire complex but not to the components may be used to screen cells for formation of complex, thus are useful in assessing invasive potential. Such as used herein, the term "an antibody that will specifically bind to the complex" refers to an antibody, monoclonal, polyclonal, immuno-active fragment thereof or single chain antibody that has binding affinity for the complex but will not bind to a single component. Preferably, one uses a monoclonal antibody. More preferably, one uses a single chain antibody.

Antibodies against the complex components and antibodies that bind to the complex can be prepared by techniques generally known in the art, and are typically generated to a purified sample of a complex component. The antibodies also can be generated from an immunogenic peptide that comprises one or more epitopes of a complex component.

More particularly, antibodies can be prepared by immunizing a mammal with a purified sample of the complex, a complex component, or an immunogenic peptide as discussed above, alone or complexed with a carrier. A preferred antigen for preparing an antibody that binds to the complex will be a cell containing such a complex on its surface. Suitable mammals include typical laboratory animals such as sheep, goats, rabbits, guinea pigs, rats and mice. Rats and mice, especially mice, are preferred for obtaining monoclonal antibodies. The antigen can be administered to the mammal by any of a number of suitable routes such as subcutaneous, intraperitoneal, intravenous, intramuscular or intracutaneous injection. Preferably immunization is by subcutaneous, intraperitoneal, or intravenous injection. The optimal immunizing interval, immunizing dose, etc. can vary within relatively wide ranges and can be determined empirically based on this disclosure. Typical procedures involve injection of the antigen several times over a number of weeks. Antibodies are collected from serum of the immunized animal by standard techniques and screened to find antibodies specific for the complex component. Monoclonal antibodies can be produced in cells which produce antibodies and those cells used to generate monoclonal antibodies by using standard fusion techniques for forming hybridoma cells. See, G. Kohler, et al., *Nature*, 256:456 (1975). Typically this involves fusing an antibody producing cell with an immortal cell line such as a myeloma cell to produce the hybrid cell. Alternatively, monoclonal antibodies can be produced from cells by the method of Huse, et al., *Science*, 256:1275 (1989).

One suitable protocol provides for intraperitoneal immunization of a mouse with a composition comprising purified complex component conducted over a period of about two to seven months. Spleen cells then can be removed from the immunized mouse. Sera from the immunized mouse is assayed for titers of antibodies specific for the complex component prior to excision of spleen cells. The excised mouse spleen cells are then fused to an appropriate homogenic or heterogenic (preferably homogenic) lymphoid cell line having a marker such as hypoxanthine-guanine phosphoribosyltransferase deficiency (HGPRT⁻) or thymidine kinase deficiency (TK⁻). Preferably a myeloma cell is employed as the lymphoid cell line. Myeloma cells and spleen cells are mixed together, e.g. at a ratio of about 1 to 4 myeloma cells to spleen cells. The cells can be fused by the polyethylene glycol (PEG) method. See, G. Kohler, et al., *Nature*, supra. The thus cloned hybridoma is grown in a culture medium, e.g. RPMI-1640. See, G. E. More, et al., *Journal of American Medical Association*, 199:549 (1967). Hybridomas, grown after the fusion procedure, are screened such as by radioimmunoassay or enzyme immunoassay for secretion of antibodies that bind to the complex component. Preferably an ELISA is employed for the screen. Hybridomas that show positive results upon such screening can be expanded and cloned by limiting dilution method.

In accordance with this invention, antibodies against complex components and antibodies that bind to the complex can be used as probes for detection.

The probes, e.g., antibodies, can be labelled directly with a reporter or indirectly with a member of a specific binding pair using conventional techniques.

Specific binding pairs can be of the immune or non-immune type. Immune-specific binding pairs are exemplified by antigen-antibody systems of hapten/anti-hapten systems. These include fluorescein/anti-fluorescein, dinitrophenyl/anti-dinitrophenyl, biotin/anti-biotin, peptide/anti-peptide and the like.

Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugated chemistries. Biotin can be covalently coupled to antibodies by utilizing commercially available active derivatives. Some of these are biotin-N-hydroxy-succinimide which binds to amine groups on proteins; biotin hydrazide which binds to carbodiimide coupling; and biotin maleimide and iodoacetyl biotin which bind to sulfhydryl using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-2-(dimethyl-aminopropyl)carbodiimide (EDAC).

Homobifunctional crosslinkers, including the bifunctional imidoesters and bifunctional N-hydroxy-succinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sufdhydryl reactive group as the second functional group, and a sufdhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labelled probe, e.g., antibody, detactably-labelled antibodies, or detectably-labelled member of the specific binding pair is coupled to a reporter which can be a radioactive isotope, enzyme, fluorogenic, chemiluminescent or electrochemical materials. Two commonly used radioactive isotopes are $^{125}I$ and 3H. Standard radioactive isotopic labelling procedures include the chloramine T, lactoperoxidase and Bolton-Hunter methods for $^{125}I$ and reduction methylation for $^3H$.

Enzymes suitable for use in this invention include, but are not limited to, horseradish peroxidase, alkaline phosphatase, β-galactosidase, glucose oxidase, luciferase, β-lactamase, urease and lysozyme. Enzyme labelling is facilitated by using dialdehyde, carbodiimide coupling, homobifunctional crosslinkers and heterobifunctional crosslinkers as described above for coupling an antibody with a member of a specific binding pair.

The labelling method chosen depends on the functional groups available on the enzyme and the material to be labelled, and the tolerance off both to the conjugation conditions. The labelling method used in the present invention can be one of, but not limited to, any conventional methods currently employed including those described by Engvall and Pearlmann, *Immunochemistry*, 8:871 (1971), Avrameas and Ternynck, *Immunochemistry*, 8:1175 (1975), Ishikawa, et al., *J. Immunoassay*, 4(3):209–237 (1983) and Jablonski, *Anal Biochem.*, 148:199 (1985), which are incorporated herein by reference.

Labelling can be accomplished by indirect methods such as using spacers or other members of specific binding pairs. An example of this is the detection of biotinylated antibody with unlabelled streptavidin and biotinylated enzyme, with streptavidin and biotinylated enzyme being added either sequentially or simultaneously. Thus, according to the present invention, the antibody used to detect can be detectably-labelled directly with a reporter or indirectly with a first member of a specific binding pair. When the antibody is coupled to a first member of a specific binding pair, then detection is effected by reacting the antibody-first member of a specific binding complex with the second member of the binding pair which is labelled or unlabelled as mentioned above.

Moreover, the unlabelled detector antibody can be detected by reacting the unlabelled antibody with a labelled antibody specific for the unlabelled antibody, Such an anti-antibody can be labelled directly or indirectly using any of the approaches discussed above. For example, the anti-antibody can be coupled to biotin which is detected by reacting with the streptavidin-horseradish peroxidase system discussed above.

One preferred embodiment utilizes biotin. The biotinylated antibody is in turn reacted with streptavidin-horseradish peroxidase complex. Orthophenylenediamine, 4-chloronaphthol, or tetramethylbenzidine (TMB) can be used to effect chromomgenic detection.

The preferred immunoassay format for practicing this invention is a forward sandwich assay in which the capture reagent has been immobilized, using conventional techniques, on the surface of the support.

Compounds which interact with a component of the complex may be selected by contacting a target cell having a plasminogen activator receptor with the plasminogen activator, the plasminogen activator inhibitor and the test compound. The effect of the test compound on the formation of the complex is measured by comparing target cell stiffness, migration capacity or invasive capacity before and after contact with the test compound.

The presence of the complex or a cell can be inferentially measured by looking at cytoskeletal stiffness.

Changes in cytoskeletal stiffness can be measured directly or indirectly using a number of techniques familiar to the skilled artisan.

One technique that can be used to measure cytoskeletal stiffness directly is the use of a twisting magnetic cytometer in which controlled mechanical forces can be applied directly to cell surface molecules via specific ligand-coated ferromagnetic microbeads [Wang, et al., *Science*, 260:1124–1127 (1993)]. Briefly, target cells, for example, human myogenic cells are isolated, passaged and cultured as described [Quax, et al., supra (1992)]. Cells are then plated on FN-coated 96 well dishes ($2\times10^4$ cells/well) (Removawells, Immunon II) using published methods [Quax, et al., supra (1992)]. Ferromagnetic beads (5.5 µm diameter) are coated with appropriate ligand (50 µg/ml) using a carbonate buffer absorption technique [Ingber, *Proc. Natl. Acad. Sci. U.S.A.*, 87:3579 (1990)]. In general, purified ECM molecules and anti-integrin antibodies, anti uPAR antibodies, anti uPA antibodies, anti-$PAI_1$ antibodies, and corresponding antigens, can be obtained from commercial suppliers (Collaborative Research, Tellos, Biosource, American Diagnostica).

After cell culture for 10 to 20 hours, unattached cells are removed by washing and $6\times10^4$ microbeads are added per well (about 3 beads per cell). After 10–15 min., attached cells are washed free of unbound beads. Alignment of adherent beads magnetic moment can then be produced by a brief (10 µs) and strong (1000 gauss) homogeneous magnetized field (the beads do not physically rotate because of homogeneous field). After 10–20 sec., another much smaller homogeneous field is applied for 1 min. perpendicular to the direction which the beads had been magnetized. The change in remnant field signal over time in response to this twisting field and hence, the angular strain of bead is measured using the magnetometer. Stiffness is the ratio of applied of stress to angular strain. After the cells are twisted once, if desired, compounds to be tested are added for a set period of time, e.g., 1 to 60 min. The cells are then twisted again. The difference in cytoskeletal stiffness before and after the compound addition will reflect its effect on cytoskeletal stiffness.

Cytoskeletal stiffness may also be measured using micropipette aspiration [Reviewed in R. M. Hochmuch and R. E. Waugh, *Ann. Rev. Physiol.*, 49:209 (1987)]. In this technique, one micropipette (1–5 µm diameter) with a vacuum pressure is used to hold one side of the cell. Another micropipette (1–5 µm diameter) with a vacuum pressure is attached to the opposite side of the cell and is used to deform the cell by moving the 2nd pipette away from the cell. The cytoskeletal stiffness is gauged by the force necessary to move the pipette.

Cell poking [N. O. Peterson, et al., *Proc. Natl. Acad. Sci. U.S.A.*, 79:5327 (1983)] is another technique useful in measuring cytoskeletal stiffness. In this technique, a fine glass needle (2 µm diameter) is used to indent the cell through the cell surface, stiffness can be quantitated with a known applied force and a measured deformation on the cell surface.

Cell pulling [E. Evans, "Handbook of Biophysics," Vol. 1., 1993; R. Lipowsky and E. Sachma eds. (in press)], is a modified micropipette aspiration technique, and also uses two micropipette. However, the second pipette is attached to a red blood cell membrane which is used as a strain gauge. A microbead, which is coated with specific ligands for a cell receptor, is attached firmly to the RBC membrane. In use, the whole system of the second pipette is moved toward the cell surface via a micromanipulator, once the beads attaches the cell surface, the bead is pulled away from the cell, the strain and the force can be quantitated and thus the stiffness can be measured.

Cytoskeletal stiffness can also be measured by use of a viscometer. An increase in viscosity evidences an increase in stiffness.

The present inventors have discovered and shown that cytoskeletal stifness is related to a number of functions, e.g., cellular motility, invasion and adhesion. Therefore, variations in these functions can be used to indirectly measure changes in cytoskeletal stiffness. For example, cellular motility can be measured using visual assays such as time-lapse cinematography, 3-dimensional gel migration [P. H. A. Quax, et al., *Develop. Biol.*, supra]. Centrifugation can be used to measure cell adhesion surfaces. Resistance to shear flow can also be used to measure cell adhesion by counting how many cells are still left on the surface under a given shear stress. Alternatively, cytoskeletal stiffness and formation can be used to measure changes in cellular motility, adhesion and invasiveness.

The invasive potential of a cancer cell is extremely important. In addition, changes in motility, adhesion and invasive potential are all extremely important in determining changes in the malignancy of particular tissues, tumors, etc. In one embodiment, one can determine such changes in cells by looking directly at the presence or absence of complex or indirect indications of this such as looking at changes in cytoskeletal stiffness. For example, one can use an in vitro assay where one takes a cell of interest, plates it, treats the cell with a compound that interacts with a complex, for example, a compound that interacts with the inhibitor component such as antibody to an inhibitor and then assess the cytoskeletal stiffness. Those cells which are responsive to the blocking and thus, show an increase in stiffness have a higher invasive potential. This assay can then be used to measure changes in particular tissues over time by looking at changes of any and subsequent assays.

Similarly, one can use a probe for the complex to screen in vivo for the presence of the complex. Thus by injecting a probe such as an antibody to the complex determining where the binding has occurred and the amount of binding, one can discover presence of complex, changes such as increases in formation or decreases in formation of complex to determine if the cells are acting in an invasive manner. Preferably, the probe will be bound to a radionucleotide that can readily be screened by use of a gamma camera. Alternatively, one can use these probes in vitro to screen tissue or sera for complex.

Another embodiment of the present invention provides a method that can be used both in vitro and in vivo to regulate cytoskeletal stiffness and thus regulate functions related to the cytoskeleton, such as cell adhesion, motility, migration, proliferation and differentiation.

The compounds can be contacted with a target cell by any known means. For example, the compound may be directly administered to a target cell in culture. When the target cell is in vivo, the compound may be administered by any of a variety of means, for example, parenteral injection (intramuscular (I.M.), intraperitoneal (I.P.), intravenous (I.V.), intracranial (I.C.) or subcutaneous (S.C.)), oral, inhaling through airways, or other known routes of administration. Parenteral injection is typically preferred.

The compounds can be administered in any means convenient, for example, it can be mixed with an inert carrier such as sucrose, lactose or starch. It can be in the form of tablets, capsules and pills. For parenteral administration, it will typically be injected in a sterile aqueous or non-aqueous solution, suspension or emulsion in association with a pharmaceutically-acceptable parenteral carrier such as physiological saline.

According to the present invention, an "effective amount" of a compound which interacts with a component of the complex is an amount sufficient to achieve the desired change in target cell cytoskeletal stiffness. It will be appreciated that the actually preferred amounts of compounds used will vary according to the specific compound being utilized, the particular compositions formulated and the mode of administration.

For example, to inhibit formation of the complex, compounds are added to result in a concentration from 1 μg/ml–500 μg/ml. Preferably, 2 μg/ml—10 μg/ml. More specifically, antibodies against the complex components are added to result in a concentration from a 1 μg/ml to 100 μg/ml. Complex component antagonists or competitors, e.g., ATF, are added to result in a concentration from 1 nM to 100 nM. For in vivo application, it will be appreciated that the effective amount will vary according the compound being utilized and the mode of administration.

As aforesaid, the method of the present invention is reversible in that the compound(s) may reversibly interact with a component of the complex. For example, the effective concentration of a compound may be decreased by dilution, or may be removed by washing the culture. Additionally, competitors of the compound may be added to reverse its action. Compounds, such as antibodies, may be designed to decrease binding affinity under certain conditions, e.g., salt concentration. By use of a compound that reversibly interacts with the component of the complex, CSK stiffness may be reversibly regulated.

When the method of the present invention is used, for example, in in vitro cell culture to detach adherent cells, an effective amount of a compound is added such that a decrease in cytoskeletal stiffness results. Thereafter, one can use a mild reagent such as a rinse to detach the cells from the surface of a culture plate. Alternatively, there are times when an increase in cytoskeletal stiffness is desired for a tissue culture. This can readily be accomplished by adding compounds to decrease formation of complex, such as antibodies against activator and inhibitor.

Stiffened target cells produced in accordance with the present invention may be used to select compounds, including drugs, that reverse cytoskeletal stiffness and thus may be useful as agents for increasing cellular motility.

One can take a stiffened target cell, wherein the complex has been formed, add a test compound and measure to see if there is any change in stiffness. This assessment can be made by any standard technique. For example, typically one would have a control to which another substance was added and which was kept at similar conditions and measured at the same time. The results are then compare with the test cell.

The present invention further include methods for screening and selecting compounds that interact with the formation of the complex and thus may be used to regulate cytoskeletal system. This method involves adding the components necessary to form the complex plus an additional compound which is the test compound. One then determines whether or not the complex has been formed by standard techniques such as measuring the stiffness of the cell. The effect of the test compound would be measured by comparing the stiffness or complex formation, for example, by using a probe for the complex against a control group. For example, same components were added under the same conditions and in the same amounts and tested at the same time without the addition of the compound being screened. Any changes in formation of the complex or changes in cytoskeletal stiffness would indicate that the compound interacts with formation of the complex. If one is just measuring cytoskeletal stiffnes and if one determines a change in cytoskeletal stiffness, you would then want to directly look at the effect of that compound on the formation of complex in order to confirm that it did interact with the complex, and not some other element that may also influence cytoskeletal stiffness.

By regulating cytoskeletal stiffness, the method of the present invention can be used to control cell growth, adhesion, motility, invasion, mitosis and differentiation, and therefore can be used to treat disorders in which regulation of these functions would benefitted. Functions that are deregulated could be re-regulated by modulating cytoskeletal stiffness.

It has been shown that the urokinase inhibitor (P. A. Sappino, personal communication), PAI, is on the side of the uterus and urokinase and the receptor are on the surface of the embryo. Accordingly, inhibition of the complex may also be useful as a means for contraception.

The method of the present invention may also be useful in treating disorders involving inflammation, such as asthma and bronchitis. A hallmark of the inflammation process is the migration of neutrophils and macrophages to the peripheral tissue. By stiffening these cells, their movement out of the blood vessel can be impeded, and the inflammation inhibited.

The method of the present invention may also be useful in speeding up wound healing. By downregulating cytoskeletal stiffness and enhancing the formation of the complex, cell migration could be speeded up and the wound could be healed faster, similarly, up or downregulation of the complex could be used to modulate mechanical properties of tissues, either directly through changing mechanical properties of cells, or, indirectly by changing the rate that motile cells secrete extracellular matrix.

The present invention is further illustrated by the following examples. These examples are provided to aid in the understanding of the invention and are not construed as a limitation thereof.

The references cited above and below are herein incorporated by reference.

EXAMPLE 1

Linkage Between the uPA Receptor and the CSK

Human myogenic satellite cells were cultured according to a previously described method [P. H. A. Quax, et al. *Develop. Biol.*, supra]. Briefly, muscle biopsies obtained from orthopedic surgery were digested in 0.15% pronase in PBS for 1 hour at 37° C. After centrifugation and washing, the cells were seeded at $6 \times 10^4$ cells per 25 cm$^2$ flask in HamF12 medium containing 20% fetal calf serum, 2 mM glutamine, 100 U/ml penicilin and 100 µg/ml streptomycin. The expression of desmin was tested for a specific marker of the myogenic lineage using a standard immunoperoxidase procedure. For all experiments passage one or passage two cell cultures were used.

To explore the existence of a direct mechanical linkage between the uPAR and the CSK, the recently described magnetic twisting cytometry technique [N. Wang, et al., *Science*, 160:1124 (1993)] was used to apply controlled mechanical stresses directly to surface receptors of myogenic cells. Briefly, ferromagnetic microbeads (5.5 µm diameter, 1 mg/ml) were coated with different ligands (RGD, uPA, or AcLDL, all at 50 µg/ml) in a carbonate buffer stored at 4° C. overnight to facilitate protein absorption onto the beads [D. E. Ingber, *Proc. Natl., Acad. Sci. U.S.A.*, supra]. Human myogenic cells were plated at $2 \times 10^4$ cells per well on fibronectin-coated plastic dishes (96-well Removawells, Immunolon II) for 10–20 hours before experiments. Beads were added to a well for 10 min. and then the unbound beads were washed away with medium. Mechanical measurements were performed as follows: all beads were first magnetized in one direction and then twisted in a perpendicular direction. The twisting magnetic field imposed a torque and thus shear stress on the beads and through the beads to the cells. Stress was calibrated [N. Wang, et al., *Science*, supra] and angular strain was measured as the beads rotated in place in response to stress. Since angular strain is a measure of deformation, it reflects changes in average magnetic signals per bead, and thus does not depend on the number of beads per cell, or total bead number. Stiffness (ratio of stress to strain) is a measure of the resistance of the cells to applied stress.

Figure 1:
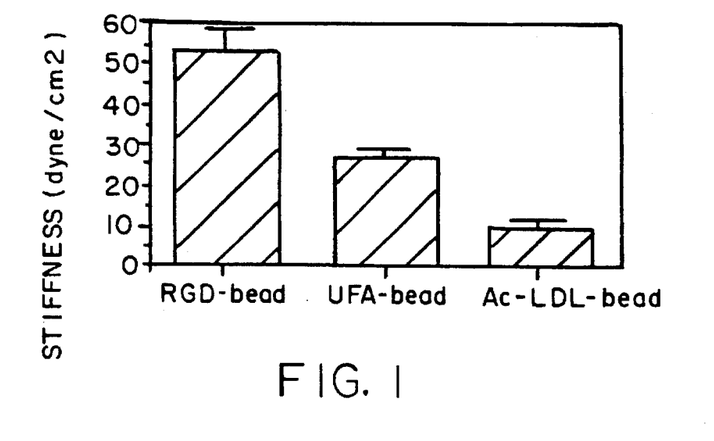
FIG. 1 is a bar graph showing the stiffness (ratio of stress to strain) of living cells measured under different conditions. Stress and strain were determined as described [N. Wang, et al., Science, 260:1124 (1993)]. Stiffness was measured with different ligand-coated beads when 40 dyne/cm$_2$ of stress was applied: RGD, Arg-Gly-Asp-containing synthetic peptide; uPA, urokinase plasminogen activator; Ac-LDL, acetylated-low density lipoprotein.
Figure 2:
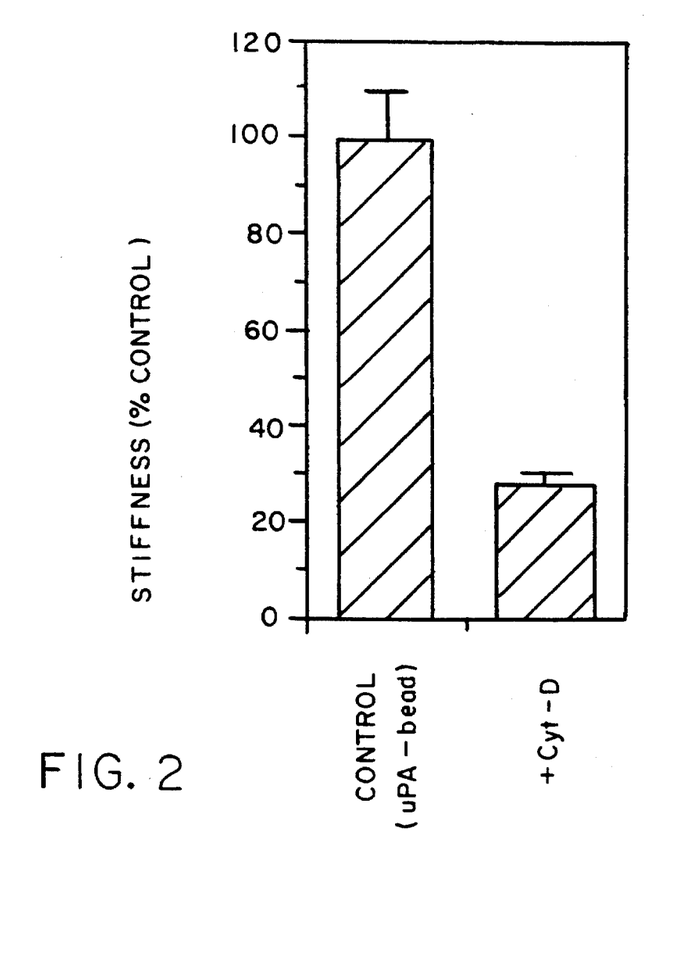
FIG. 2 is a bar graph showing stiffness measured with uPA coated beads at 40 dyne/cm$^2$ of applied stress: CONTROL, before drug treatment; +Cyt-D, after adding 1 μg/ml cytochalasin D for 15 min.
Figure 3:
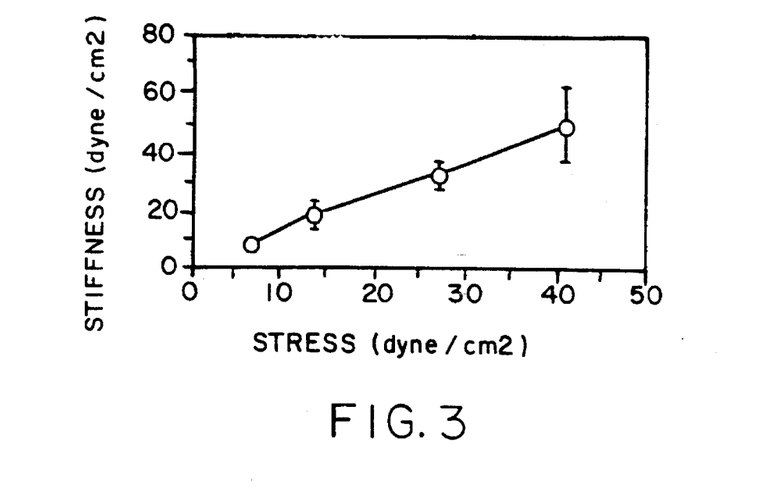
FIG. 3 is a bar graph showing the stiffening response of cells bound to uPA coated beads as stress was increased from 7 to 40 dyne/cm$^2$. Error bars=SEM.

The degree to which the urokinase receptor could provide a specific molecular pathway for mechanical force transfer to the CSK was examined. Cell response was measured to mechanical stresses, using either specific or non-specific ligand coated ferromagnetic beads. When 40 dyne/cm$^2$ with uPA coated beads the stiffness of the cells was 27 dyne/cm$^2$. In contrast, at the same applied stress the stiffness was 55 dyne/cm$^2$ with RGD (Arg-Gly-Asp) coated beads and was 10 dyne/cm$^2$ with AcLDL (acetylated low density lipoprotein) coated beads. Both RGD and AcLDL bind to specific transmembrane receptors. However, the former binds to integrins, which are known to transfer mechanical forces effectively across the cell membrane and through the cytoskeleton; in contrast the latter binds to scavenger receptors that are not involved in cell adhesion and do not transfer mechanical force to the cytoskeleton lattice [N. Wang, et al., *Science*, supra]. The fact that stiffness measured with uPA coated beads was 50% of that of RGD coated beads and was 2.7 times that of AcLDL coated beads suggest the existence of a direct mechanical linkage from the uPAR to the CSK. To further test this possibility, cells bound to uPA coated beads were then treated with cytochalasin D (1 µg/ml) for 15 min. to disrupt actin microfilaments whereupon, compared with control, a 70% decrease in stiffness was observed (FIG. 2). This was similar to the decrease in stiffness (with cytochalasin D) measured through integrin receptors (N. Wang, et al., *Science*, supra]. The existence of mechanical linkage between uPAR and the CSK was supported still further by the stiffening response of the CSK to applied stressed with uPA coated beads: when applied stress was increased from 7 to 40 dyne/cm$^2$, a proportional increase in stiffness was observed (FIG. 3). RGD coated beads also induced a similar stiffening response, i.e., the slope of stiffness versus stress was almost identical when measured with RGD beads compared to that measured with uPA beads (data not shown). The stiffening response was also observed with RGD beads in endothelal cells (N. Wang, et al., *Science*, supra].

To test the specificity of uPA coated beads binding to uPAR cells were preincubated with either 6 nM soluble ATF (the amino terminal fragment of uPA that competes with uPA for binding of uPAR but has no enzymatic activities) or 5 µg/ml soluble monoclonal antibodies against uPAR for 10 min. to compete for the binding site of uPAR before addition of uPA coated beads. Effective inhibition of uPA coated bead binding to the cell surface was observed. Preincubating with 100 µg/ml of a soluble synthetic peptide GRGDSP (Gly-Arg-Gly-Asp-Ser-Pro), known as a competitor for binding of integrin receptors, had no inhibitory effects on bead binding to cells and on CSK stiffness with uPA coated beads. These results strongly suggest that occupancy of integrins does not inhibit mechanical force transfer from the uPAR to the CSK, and thus establish uPAR as a novel mechanotransducer.

EXAMPLE 2

Inhibition of Complex Formation

Figure 4:
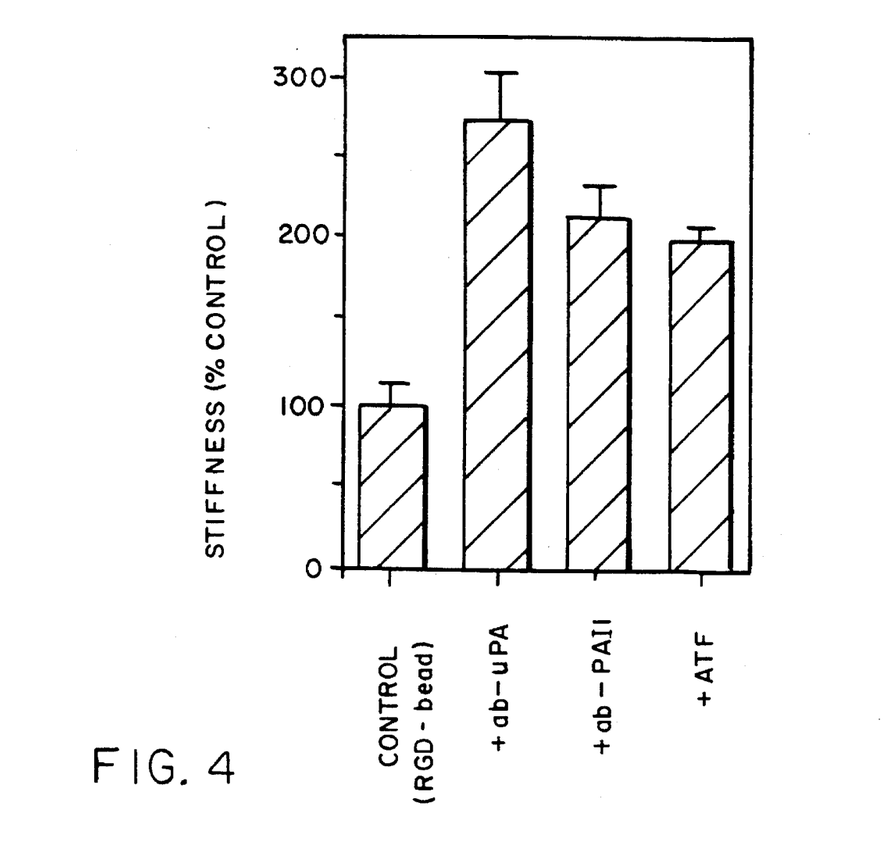
FIG. 4 is a graph showing the stiffness measured with RGD coated beads at 40 dyne/cm$^2$ of applied stress before and after addition of antibodies or ATF against urokinase receptor, urokinase, or urokinase inhibitor. CONTROL, before antibody or ATF treatments; +ab-uPA, after adding monoclonal antibodies against urokinase (5 μg/ml) for 15 min.; +ab-uPAI$_1$, after adding monoclonal antibodies against urokinase inhibitor (5 μg/ml) for 15 min.; +ATF, after adding an amino terminal fragment of uPA (6 nM) for 15 min.; ATF competes with uPA for receptor binding but is enzymatically inactive. Error bars=SEM.

If the complex of uPAR, uPA, and uPA inhibitor (PAI$_1$) were a mechanotransducer, interfering with its formation might change force transfer through it, and thus might modify CSK stiffness. This hypothesis was tested with RGD coated beads as a probe of CSK stiffness. The formation of the complex was prevented with soluble ATF (143 amino acids 6 nM), antibodies against uPA (5 μg/ml), or antibodies against $PAI_1$ (5 μg/ml). Preventing binding of uPA to its receptor by adding 6 nM soluble ATF in the myogenic cell culture medium resulted a 2.0 fold increase in CSK stiffness. Adding monoclonal antibodies against uPA's catalytical domain (ab-uPA) (5 μg/ml) resulted in a 2.7 fold increase in stiffness. Addition of monoclonal antibodies against $PAI_1$ (5 μg/ml, ab-$API_1$) also resulted in a 2.1 fold increase in CSK stiffness (FIG. 4).

Integrins such as $\alpha_v\beta_3$ can bind to vitronectin and have been associated with invasion [S. Belluci, et al., *Path. Biol.*, 40:779 (1992); E. Ruoslahti, *J. Clin. Invest.*, 87:1 (1991)]. $PAI_1$ is found to be associated with vitronectin [K. T. Preissner, et al., *Thromb. Hemost.* 66:123 (1991); G. J. Ciambrone, et al., *J. Cell Biol.*, 111:2183 (1990); D. Seiffert, et al., *Cell. Differ. Dev.*, 32:287 (1990)]. Thus, $PAI_1$ could be a critical part of the migration system connecting ECM with uPAR-uPA and the CSK. Thus, it is possible there exists a mechanical linkage between the complex and integrins or other cell adhesion molecules either through extracellular or intracellular pathways. Extrapolating stiffness to zero applied stress (FIG. 3), stiffness was found to be 1 dyne/$cm^2$ for uPA coated bead. This value is 15 times less than that for RGD coated beads. Stiffness at zero applied stress is a measure of cell adhesion if the cell surface molecules, through which stiffness is measured, are mechanically linked to the CSK. Thus, lower stiffness at zero stress measured through the urokinase receptor is consistent with the notion that the complex is migration system rather than an adhesion system.

While not wishing to be bound be theory, we believe that the uPAR/uPA/PAI complex has the following role in cell crawling 1) formation of the complex initiates a transient adhesion of the cell through the complex to ECM; 2) internalization of the complex [M. V. Cubellis, et al., *EMBO J.*, 9:1079 (1990)] triggers dissociation of integrins and other cell adhesion molecules from ECM and from the CSK, and permits a recycling of the complex so that a new receptor and thus a new complex will be formed at the leading edge of the cell membrane; 3) repetition of the first two steps maintains cell migration. This mechanism could explain the apparent paradox: in migrating cells, both proteolytic activities and amounts of $PAI_1$ are enhanced. The functions of $PAI_1$ appear to be not only for controlling proteolysis but also for assisting migration. When the uPAR-uPA system is not bound to $PAI_1$, it activates plasminogen and assumes the proteolytic role of invasion.

The above examples provide evidence of a novel mechanotransducer formed by the complex of uPAR-uPA-$PAI_1$ in addition to its conventional proteolytic function.

EXAMPLE 3

In Vitro Assay for Cell Invasiveness

In order to confirm the invasive potential of a carcinoma cell, the change in CSK stiffness of M7 and M6 cells before and after treatment with a urokinase antagonistic/competitor and an antibody against the urokinase $PA_1$, inhibi tor was determined.

M7 is an abbreviation for MCF-7/AZ (alternative names: MCF-7(AZ), MCF-7). M6 is an abbreviation for MCF-7/6 (alternative name: MCF-7(ML)). These cells are human cell lines derived from a breast carcinoma [H. D. Soule, et al., *J. Natl. Cancer Inst.*, 51:1409 (1973); M. E. Bracke, et al., *Br. J. Cancer*, 63:867 (1991)]. M7 cells are noninvasive cancer cells and M6 are invasive cancer cells.

M6 cells were cultured with a mixture (1/1) of Ham's F12 and Dulbecco's Modified Eagle medium supplemented with 10% FBS, 0.05% L glutamine, 250 IU/ml penicillin, and 100 μg/ml streptomycin.

M7 cells were cultured with modified minimum Essential Medium Eagle supplemented with 5% FBS, 6 ng/ml bovine insulin, 0.05% L-glutaminen 250 IU/ml penicillin, and 100 μg/ml streptomycin.

Figure 5:
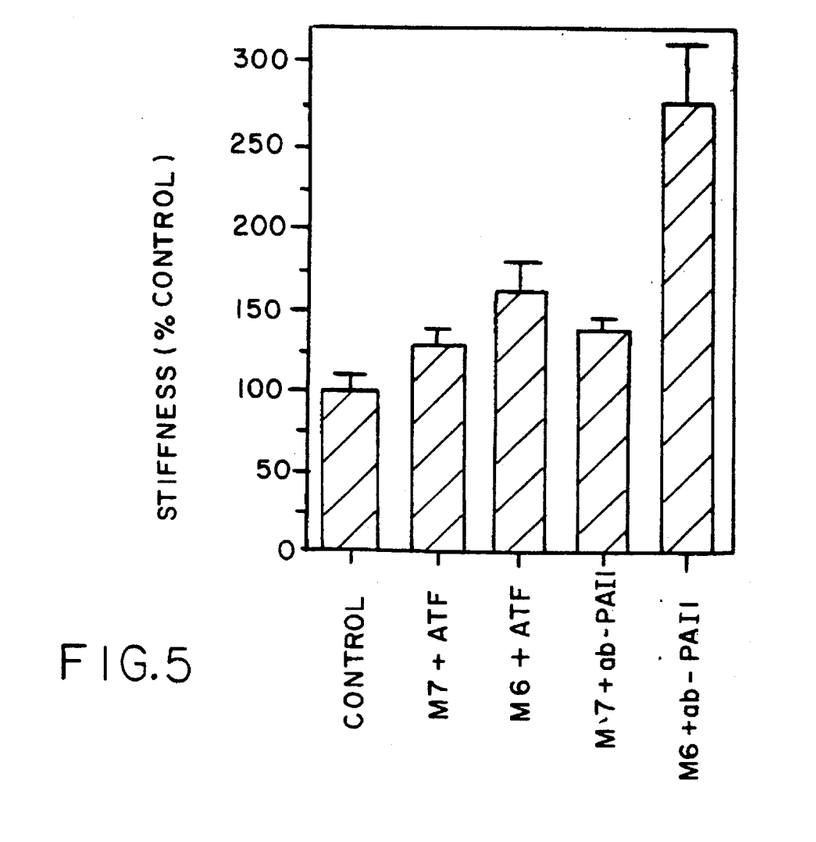
FIG. 5 is a bar graph showing stiffness of M6 (MCF-7/6) and M7 (MCF-7AZ) carcinoma cells upon addition of ATF and antibody against the $PAI_1$ inhibitor.

Both M7 and M6 cells were plated onto the 96 wells (Removawells, Immunon II, Dynatech) coated with 500 ng/$cm^2$ fibronectin at 80,000 cells/well overnight before the experiments. Ferromagnetic microbeads (5.5 μm diameter) precoated with RGD were added to the well at a concentration of 2 beads per cell. After 10 min. of bead addition, unbound beads were washed away with medium. Then the well with the cells were placed into the magnetic twisting cytometer and a given magnetic twisting field (a given twisting stress) was applied to the well such that resulting angular strain was measured. Stiffness was quantitated as the ratio of stress to strain. Then either ATF (6 nM) or monoclonal antibodies against $PAI_1$ (5 μg/ml, ab-PAI1) was added into the well. After 15 min. of ATF of ab-PAI1 addition, the same well was twisted again using the same amount of twisting stress. Stiffness was measured again. The difference in stiffness between before and after ATF or ab-PAI1 addition reflects the effects of the compound on CSK stiffness. Both ATF and ab-PAI1 increased CSK stiffness in M7 and M6 cells. ATF increased CSK stiffness by about 60% in M6 cells and about 30% in M7 cells; ab-PAI1 increased CSK stiffness by about 270% in M6 cells and only about 35% in M7 cells (FIG. 5).

As can be seen, both ATF and the antibody against $PA_1$, significantly increased CSK stiffness in the M6 invasive cell line. Thus, this assay provides a simple and rapid means for determining a cells invasive potential.

Figure 6:
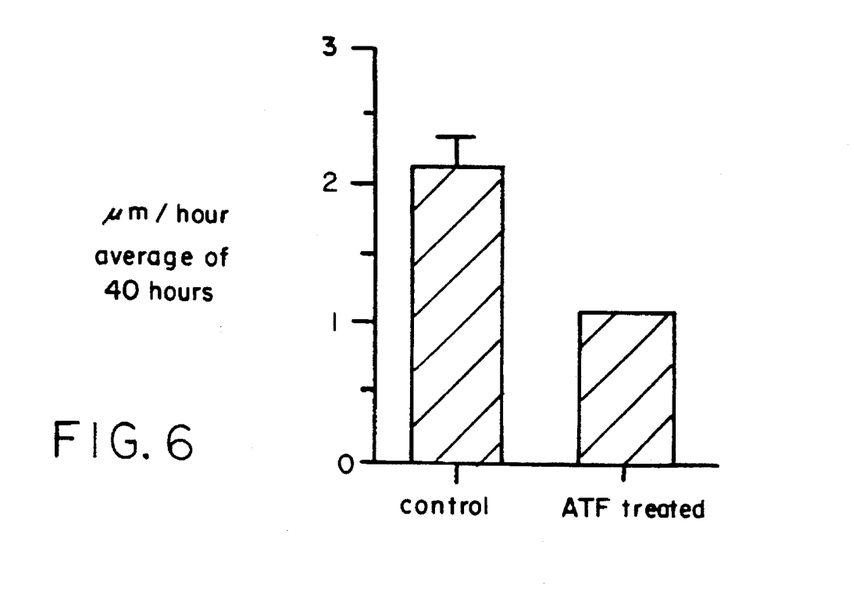
FIG. 6 is a bar graph showing migration speed of cell line M6 (MCF7/6) treated with ATF.

To measure motility or migration speed, M6 cells were cultured in chambers as described by (G. Barlovatz-Meimon, et al., in preparation). Using microcinematography the migration speed of the control [control: M6 cells, nontreated] and the treated M6 cells were compared (average of 40 hours of film). As can be seen in FIG. 6, a nearly 50% decrease in speed was observed in AFT (6 nM) treated M6 cells. (FIG. 6)

It should be understood that the examples and embodiments described herein are for illustrative purposes only and that various modifications or changes in light thereof will be suggested to persons skilled and purview of this application and the scope of the appended claims.

What is claimed is:

1. A method of screening for a test compound which has an effect on the cytoskeletal stiffness of a target cell having a plasminogen activator receptor comprising:

(a) contacting the target cell with a plasminogen activator, the plasminogen activator inhibitor and the test compound; and (b) measuring the effects of the test compound on cytoskeletal stiffness of the target cell by comparing the resulting cytoskeletal stiffness against the cytoskeletal stiffness measured when the target cell is contacted only with the plasminogen activator and the inhibitor.

2. The assay of claim 1, wherein the plasminogen activator is urokinase.

* * * * *